United States Patent [19]

Brunel

[11] Patent Number: 5,037,698

[45] Date of Patent: Aug. 6, 1991

[54] CAPSULE FILLING EMPLOYING HYGROSCOPIC COMPONENTS

[75] Inventor: Francois Brunel, Fegersheim, France

[73] Assignee: Lilly Industries Limited, Basingstoke, United Kingdom

[21] Appl. No.: 145,444

[22] Filed: Jan. 19, 1988

[30] Foreign Application Priority Data

Jan. 21, 1987 [GB] United Kingdom ............... 8701332

[51] Int. Cl.$^5$ .................. B29C 39/10; A61K 9/64; A61K 9/66

[52] U.S. Cl. ................ 428/402.2; 264/4; 424/456; 424/455; 424/451; 514/962; 514/963; 252/194

[58] Field of Search .............. 428/402.2; 424/455, 424/456; 264/4

[56] References Cited

U.S. PATENT DOCUMENTS

| | | | |
|---|---|---|---|
| 2,580,683 | 1/1952 | Kruegr | 99/165 |
| 2,667,268 | 1/1954 | Griffin | 206/84 |
| 2,990,334 | 6/1961 | Graham | 167/83 |
| 3,126,321 | 3/1964 | Kurtz | 424/455 |
| 4,002,718 | 1/1977 | Gardella et al. | 424/455 |
| 4,086,006 | 1/1978 | Moritz | 426/97 |
| 4,198,391 | 4/1980 | Grainger | 424/455 |
| 4,450,877 | 5/1984 | Walker et al. | 141/1 |
| 4,486,412 | 12/1984 | Shah et al. | 424/456 X |
| 4,695,450 | 9/1987 | Bauer et al. | 424/455 |
| 4,701,327 | 10/1987 | Henmi et al. | 424/455 |
| 4,708,834 | 11/1987 | Cohen et al. | 264/4.3 |
| 4,744,988 | 5/1988 | Brox | 424/456 |
| 4,777,048 | 10/1988 | Hersh et al. | 424/452 |
| 4,780,316 | 10/1988 | Brox | 424/455 X |
| 4,795,643 | 1/1989 | Seth | 424/455 X |
| 4,804,542 | 2/1989 | Fischer et al. | 424/456 |
| 4,892,766 | 1/1990 | Jones | 424/456 X |
| 4,948,591 | 8/1990 | Yamada | 424/456 |

FOREIGN PATENT DOCUMENTS

| | | | |
|---|---|---|---|
| 86468 | 8/1983 | European Pat. Off. | |
| 752362 | 7/1956 | United Kingdom | 81/1 |
| 1341121 | 12/1973 | United Kingdom | |

OTHER PUBLICATIONS

*Hackh's Chemical Dictionary*, 3rd ed., 765 (1944).

Primary Examiner—Richard D. Lovering
Assistant Examiner—John M. Covert
Attorney, Agent, or Firm—Douglas J. Taylor; Leroy Whitaker

[57] ABSTRACT

Capsules containing a hygroscopic or deliquescent component are stabilized by a) forming a mixture of the hydrogscopic or deliquescent compound with a sufficient quantity of water to achieve an equilibrium, b) adding a thickening agent and c) heating the solution or suspension; and introducing the heated composition so formed into the capsule. Preferably an equilibrium-protecting agent, such as glycerin, is also added.

16 Claims, No Drawings

CAPSULE FILLING EMPLOYING HYGROSCOPIC COMPONENTS

The present invention relates to a method of filling gelatin capsules with hygroscopic or deliquescent components and to compositions for use in that method.

Hygroscopic and deliquescent components pose problems when filled into gelatin capsules in that they absorb moisture from the gelatin, leaving the latter moisture depleted and often in a brittle or deformed state, susceptible to breakage and leakage. Many pharmaceutically active compounds are hygroscopic or deliquescent and, where the hygroscopicity thereof is particularly marked, they have been unsuitable for formulation in gelatin capsule form, a form recognised normally as being convenient both for the pharmaceutical formulator and patient user. Clearly, a certain degree of hygroscopicity can be tolerated or allowed for. Thus, with slightly hygroscopic products, that is products with a hygroscopicity of less than 10% water absorption at 43% relative humidity, the problem can be overcome simply by employing, for example, hydrophobic fatty excipients along with the product. It has been found, however, that this expedient does not overcome the problem when products having a greater hygroscopicity are involved.

The present invention seeks to provide a method whereby hygroscopic or deliquescent components, irrespective of the degree of hygroscopicity thereof, can be formulated for filling into gelatin capsules without subsequent problems arising from moisture transfer from the gelatin to the hygroscopic or deliquescent component.

Thus, according to the present invention there is provided a method of filling a capsule with a solid or semi-solid composition containing a hygroscopic or deliquescent component which comprises the steps of a) forming a mixture of the hygroscopic or deliquescent component with a sufficient quantity of water to achieve an equilibrium, b) adding a thickening agent and c) heating to form a solution or suspension; and introducing the heated composition so formed into the capsule, preferably a hard gelatin capsule. Preferably an equilibrium protecting agent is also added to the composition before or during the heating step.

The term "equilibrium" above is intended to denote the fact that sufficient water is present in the composition to prevent it having a deleterious effect on the integrity of the capsule shell. Thus the amount of water present may be slightly below or above the stoichiometric quantity required to form a stable hydrate, provided that, in storage, the absorption of water from, or release to the gelatin walls is low enough to prevent embrittlement or deformation.

By "equilibrium protecting agent" is meant an agent which is miscible with water and the thickening agent, or which is able to form a stable emulsion therewith, and which allows the final composition to become solid or semi-solid when cooled to room temperature.

The equilibrium protecting agent assists in providing a stable composition, in which the water-content of the hygroscopic or deliquescent component is uniformly maintained. Any substance which does not deleteriously affect the active ingredient and which is liquid or liquifiable within the range of temperatures used in preparing the composition may be considered. For pharmaceutical compositions the agent should be a pharmaceutically-acceptable substance. The agent should preferably be one in which the hygroscopic or deliquescent component is at least partially soluble. Typical of such substances are, for instance, aliphatic or aromatic hydroxy compounds such as the alcohols or the polyhydroxy compounds. A preferred class of agents are demulcents, such as glycerin. Another class of compounds includes the oils, such as mineral or vegetable oils. The oils, to be useful, should be miscible with water and with the thickening agent to produce a stable emulsion. Such oils include, for example, ARACHIDE (peanut oil) and LABRAFIL (a mixture of palm kernel oil, palm oil and PEG-6), supplied by Gattefosse.

The thickening agent may be selected from the known thermosoftening solid or semi-solid pharmaceutical excipients well known in the art. Such excipients have varying degrees of hydrophobicity or hydrophilicity. As examples of such agents may be mentioned the polyethylene glycols (PEGs), or the excipients provided by Seppic and Gattefosse under the brand names SIMUSOL, LABRASOL and LABRAFIL. SIMUSOL is an oleate, LABRASOL consists of $C_8$–$C_{10}$ ethoxylated saturated glycerides and LABRAFIL consists of a mixture of palm kernel oil, palm oil and PEG-6. Particularly suitable are the PEGs, especially those having molecular weights in the range of from 200 to 10,000. The minimum amount of PEG required in the composition will depend on its molecular weight and on the amount of water and equilibrium-protecting agent present. Those skilled in the art will readily be able to determine the quantity of a particular thickening agent required to produce a solid composition at normal temperatures. The preferred PEGs are those having a molecular weight in the range 2000 to 6000. If the molecular weight of the PEG is 2000, then it should preferably be present in an amount of at least 40%, whilst a PEG of 4000 molecular weight would require 35% or more to be present and a 6000 molecular weight PEG need be there in as little as 30% by weight. It will be appreciated that, as the thickening agent may be present in any amount above the minimum described above, the previously defined ranges for the other constituents of the composition are based on the minimum quantity of thickening agent required to produce a solid or semi-solid composition at room temperature.

The order in which the steps of producing the composition are carried out is not critical, but may be varied to suit the particular components making up the final composition which, when heated, may be a solution, an emulsion or a suspension.

The composition may be prepared, for example, by preparing a mixture of water and the equilibrium-protecting agent, agitating and adding the hygroscopic or deliquescent component. The mixture thus formed may then be heated to aid or increase dissolution and the thickening agent then added.

Alternatively the components, including the equilibrium-protecting agent and the thickening agent may be mixed together and then heated, or the hygroscopic or deliquescent component may be mixed with the required quantity of water and heated to provide a solution or suspension to which are added the remaining components.

The composition should be solid or semi-solid at normal temperatures. It may be a thermotropic or thixotropic mixture.

The temperature to which the composition is heated should be sufficient to render it flowable without being so high that it would damage the active ingredient or the capsule shell material when introduced. Thus the temperature may be in the range of from room temperature to the melting point, preferably from 60° C. to 70° C.

As will be appreciated, the hygroscopic or deliquescent component may initially be solid or liquid. Where initially solid, the water equilibration step of the invention will, in the case of a deliquescent component, result in a saturated aqueous solution of the component being formed. Hygroscopic solid components which do not deliquesce will, of course, remain solid after equilibration with water, but will be dispersed in the final composition. After heating and the addition of the thickening agent, the resulting solution, emulsion or suspension may be filled, in general along with other components, into capsules, whether of the hard gelatin or soft gelatin type, in conventional manner whilst still warm.

On cooling, the composition attains a solid or semi-solid state within the capsule. The presence of the equilibrium amount of water in the composition, optionally protected by the equilibrium-protecting agent, prevents deterioration of the capsule material by either removal of water to cause it to become brittle or by the softening of the capsule due to transfer of excess water to the gelatin from the composition.

It will be appreciated that the amount of water required by a hygroscopic or deliquescent component to overcome the problem of capsule embrittlement will vary depending on the nature of the component. It will also be appreciated that there will be a degree of tolerance in the amount of water added. It can be readily determined by those skilled in the art how little or how much water need be added to a particular hygroscopic or deliquescent component. In general, water will constitute up to about 20% of the composition.

Normally the composition will contain up to about 50% by weight of the hygroscopic or deliquescent component while the amount of water present will normally be up to about 10%, and the equilibrium-protecting agent will generally constitute up to about 15% by weight of the composition.

Typically, a capsule filling composition for use in the invention may be as follows:-

| Hygroscopic or deliquescent component | 0.1–45% by wt. |
|---|---|
| Water | 0.1–10% by wt. |
| Glycerin | 0.1–15% by wt. |
| PEG 4000 | 35% or more |

Whilst the present invention has, as its main advantage and aim the enablement of filling gelatin capsules with hygroscopic or deliquescent pharmaceutical components, it will be appreciated that it need not be a pharmaceutical component which is hygroscopic but, indeed, that the method of the present invention can be used to enable any desired hygroscopic or deliquescent component to be contained in a formulation, whether pharmaceutical or otherwise, for filling into a gelatin capsule. Examples of such substances include sodium or magnesium chloride, chloral hydrate, cefalexin hydrochloride, sodium valporate or citroflavinoid salts.

Since, as mentioned previously, with components with a hygroscopicity of less than 10% water absorption at 43% relative humidity, problems arising from their hygroscopicity can be overcome or masked by merely employing a hydrophobic fatty excipient along with the component, the method of the present invention has particular advantage in the filling of capsules with components with a hygroscopicity of greater than 10% water absorption at 43% RH, and still more particular advantage in the filling of capsules with deliquescent components.

The invention also provides a composition for filling into a gelatin capsule and a gelatin capsule filled with a composition comprising a hygroscopic or deliquescent component, which component is substantially saturated with water.

The invention is illustrated by the following example which relates to the filling of hard gelatin capsules with Magnesium Chloride.

EXAMPLE

| Ingredient | wt % |
|---|---|
| Magnesium chloride | 45 |
| Water | 6 |
| Glycerine | 12 |
| PEG 4000 | 37 |

The magnesium chloride and water were mixed in a beaker and heated. Glycerin was then added to the resulting suspension and the mixture stirred continuously. Finally the PEG 4000 was added, and the stirred mass kept at a temperature sufficient to maintain it in a pourable condition for introduction into the gelatin capsules, using standard capsule-filling apparatus.

The stability of capsules of the invention was determined by storing samples of capsules as prepared in the Example. The capsules were stored for 6 months at temperatures of 4° C., 20° C., 35° C. and 45° C. The capsules were found to be stable during this period under these storage conditions.

We claim:

1. A method of preparing a stable gelatin capsule containing a solid or semi-solid composition having a hygroscopic or deliquescent component which consists essentially of the steps of:

a) forming a mixture of the hygroscopic or deliquescent component with a sufficient quantity of water to achieve an equilibrium between the water and the hygroscopic or deliquescent component, adding a thickening agent, heating the solution or suspension; and b) introducing the heated composition so formed into the gelatin capsule so as to provide a gelatin capsule having reduced susceptibility to subsequent water transfer from the capsule gelatin to the hygroscopic or deliquescent component.

2. A method of claim 1 wherein the capsule is a hard gelatin capsule.

3. A method of claim 1 wherein the thickening agent is a polyethylene glycol.

4. A method of claim 3 wherein the polyethylene glycol has a molecular weight in the range of from 200 to 10,000.

5. A method of claim 4 wherein the polyethylene glycol has a molecular weight in the range of from 2000 to 6000.

6. A method of preparing a stable gelatin capsule containing a solid or semi-solid composition having a hygroscopic or deliquescent component which consists essentially of the steps of:

a) forming a mixture of the hygroscopic or deliquescent component with a sufficient quantity of water to achieve an equilibrium between the water and the hygroscopic or deliquescent component, adding a thickening agent, heating the solution or suspension; adding an equilibrium protecting agent selected from the group consisting of aliphatic or aromatic hydroxy or polyhydroxy compounds, mineral oils or vegetable oils; and b) introducing the heated composition as formed into the gelatin capsule so as to provide a gelatin capsule having reduced susceptibility to subsequent water transfer from the capsule gelatin to the hygroscopic or deliquescent component.

7. A method of claim 6 wherein the capsule is a hard gelatin capsule.

8. A method of claim 6 wherein the thickening agent is a polyethylene glycol.

9. A method of claim 8 wherein the polyethylene glycol has a molecular weight in the range of from 200 to 10,000.

10. A method of claim 9 wherein the polyethylene glycol has a molecular weight in the range of from 2000 to 6000.

11. A method of claim 6 wherein the equilibrium protecting agent is glycerin.

12. A method of claim 11 wherein the thickening agent is a polyethylene glycol.

13. A method of claim 12 wherein the polyethylene glycol has a molecular weight in the range of from 200 to 10,000.

14. A method of claim 13 wherein the polyethylene glycol has a molecular weight in the range of from 2000 to 6000.

15. A gelatin capsule filled by the method of claim 1.

16. A gelatin capsule filled by the method of claim 6.

* * * * *